US006756032B1

(12) United States Patent
Tepper et al.

(10) Patent No.: US 6,756,032 B1
(45) Date of Patent: Jun. 29, 2004

(54) METHOD TO ENHANCE AND/OR PROLONG THE EFFECTS OF A PRIMARY CHALLENGE TO A RESPONSIVE SYSTEM WITH A SECONDARY CHALLENGE

(75) Inventors: Bruce Ernest Tepper, Cincinnati, OH (US); Susan Baldwin, Cincinnati, OH (US); Scott Edward Osborne, Middletown, OH (US); Mauricio Odio, Gahanna, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/614,669

(22) Filed: Jul. 12, 2000

(51) Int. Cl.[7] .............................. A61B 10/00; C12Q 1/02
(52) U.S. Cl. ........................ 424/9.8; 424/9.81; 435/29; 530/859; 600/306; 600/307; 600/556
(58) Field of Search ................................. 424/9.8, 9.81; 435/29; 530/859; 600/306, 307, 556

(56) References Cited

U.S. PATENT DOCUMENTS

| | | | | |
|---|---|---|---|---|
| 5,935,581 A | * | 8/1999 | Kapadia et al. .......... | 424/195.1 |
| 5,939,046 A | * | 8/1999 | Halliday et al. ........... | 424/9.81 |
| 6,008,007 A | * | 12/1999 | Fruehauf et al. .............. | 435/29 |
| 6,022,896 A | | 2/2000 | Weinkauf et al. ........... | 514/557 |
| 6,060,612 A | | 5/2000 | Hong et al. .................... | 554/61 |
| 6,074,998 A | | 6/2000 | He et al. ..................... | 510/155 |

FOREIGN PATENT DOCUMENTS

| | | |
|---|---|---|
| EP | 0 749 754 A2 | 12/1996 |
| EP | 0 749 755 A2 | 12/1996 |
| GB | 636 606 A | 5/1950 |
| WO | WO 97/44066 A1 | 1/1997 |
| WO | WO 98/22147 A1 | 5/1998 |

OTHER PUBLICATIONS

Fernstrom, Acta Derm. Venereol., 34, 203–215, 1954.*
M. H. Beers & R. Berkow (Eds.) "The Merck Manual of Diagnosis and Therapy" 1999, Merck Research Laboratories, Whitehouse Station, NJ, US XP002208497; ISBN: 0–911910–10–7; pp. 786–789, p. 786, Chapter CONTACT Dermatitis; p. 788, left–hand column.
M. H. Beers & R. Berkow (Eds.) "The Merck Manual of Diagnosis and Therapy" 1999, Merck Research Laboratories, Whitehouse Station, NJ, US XP002208498; pp. 804–807; p. 804, right–hand column, chapter YEAST Infections—p. 806.
Zugerman C. et al. "Allergic Contact Dermatitis Secondary to Nitroglycerin in Nitro–Bidointment"; CONTACT Dermatitis, Munksgaard, DK, vol. 5, No. 4, 1979, pp. 270–271; XP002066217; ISSN: 0105–1873; the whole document.

Bondesson L. et al. "Inhibitory Effect of Vasoactive Intestinal Polypeptide and Ketanserin on Established Allergic Contact Dermatitis in Man"; Acta Dermato–Venereologica, XX, XX, vol. 76, No. 2, Mar. 1996, pp. 102–106; XP 000952952; ISSN: 0001–5555; abstract, figure 1, p. 105, paragraph DISCUSSION.

Peter H. Scheuber et al. "Skin Reactivity of Unsensitized Monkeys Upon Challenge with Staphylococcal Enterotoxin B: A New Approach for Investigating the Site of Toxin Action"; Infection and Immunity, American Society for Microbiology, Washington, US, vol. 50, No. 3, Dec. 1985, pp. 869–876; XP002171579; ISSN: 0019–9567; p. 870, paragraph Direct Skin Test; p. 872, right–hand column, last paragraph–p. 873, left–hand column, line 15; p. 873, right–hand column, last paragraph–p. 875, left–hand column, line 3; p. 875, left–hand column, last paragraph–p. 876, left–hand column, line 8.

Peng A et al. "Cross–Reactivity of Skin and Serum Specific IgE Responses and Allergen Analysis for Three Mosquito Species with Worldwide Distribution" Journal of Allergy and Clinical Immunology, Mosby—Yearly Book, Inc., US, vol. 100, No. 2, 1997, pp. 192–198; XP002098985; ISSN: 0091–6749; abstract, figures, p. 196, paragraph DISCUSSION—p. 197.

(List continued on next page.)

*Primary Examiner*—David Saunders
(74) *Attorney, Agent, or Firm*—Kirsten K. Stone; Eileen L. Hughett; Caroline Wei-Berk

(57) ABSTRACT

The present invention relates to a method comprising subjecting a test site of a responsive system to a primary challenge; subjecting the same test site to a secondary challenge, wherein the secondary challenge is designed to enhance and/or prolong a response of the responsive system to the primary challenge, without confounding the response nor altering the mechanism by which the primary challenge elicits a response from the responsive system; and assessing the response subsequent to the secondary challenge. The methods claimed herein also preferably comprise the additional step(s) of subjecting test site(s) to one or more pre-challenge intervention(s) and/or post-challenge intervention(s) and/or concurrent-challenge intervention(s). The methods of the present invention are also useful in a study design, also claimed herein, wherein the study comprises the steps of the method outlined above in addition to comprising the steps of creating one or more controls selected from the group consisting of negative controls, primary controls, secondary controls, positive controls, and mixtures thereof. The use of the novel methods described herein often significantly shorten the duration of and/or number of subjects needed for studies aimed at understanding the etiology of a disease and/or the ability of a intervention or challenge to prevent, cure, heal, and/or reduce and/or induce damage or injury to a responsive system.

15 Claims, No Drawings

OTHER PUBLICATIONS

Proksch E "Bedeutung der Permeabilitätsbarriere der Haut für das irritativ–toxische und das allergische Kontaktekzem (Significance of epidermal) permeability barrier in irritant and allergic contact dermatitis)"; Allergologie, Dustri Verlag, Muenchen–Deisenhofen, DE, vol. 8, No. 17, Aug. 1, 1994, pp. 346–349; XP 002076342; ISSN: 0344–5062; p. 348, left–hand column, last paragraph–right–hand column.

Steinmann A et al. "Allergic Contact Dermatitis from Black Cumin (Nigella Sativa) Oil After Topical Use" CONTACT Dermatitis, Munksgaard, DK, vol. 36, No. 5, 1997, pp. 268–269; XP000964541; ISSN: 0105–1873; the whole document.

Lundeberg L et al. Serotonin in Human Allergic Contact Dermatitis. An Immunochistochemical and High–Performance Liquid Chromatographic Study; Archives of Dermatological Research, Springer, International, Berlin, DE, vol. 291, No. 5, May 1999, pp. 269–274; XP 000952937; ISSN: 0340–3696; p. 470, left–hand column, paragraph TESTPROCEDURE.

* cited by examiner

METHOD TO ENHANCE AND/OR PROLONG THE EFFECTS OF A PRIMARY CHALLENGE TO A RESPONSIVE SYSTEM WITH A SECONDARY CHALLENGE

FIELD OF THE INVENTION

The present invention relates to test methods that can be used for clinical and non-clinical fundamental research and/or other studies to determine the consequences of a challenge to a responsive system, such as to determine the efficacy of an action, substance and/or product to prevent, induce, reduce or heal disease or injury to a responsive system. By using germane challenges to the specific responsive systems, the present invention of using a secondary challenge to enhance and/or prolong the effects of a primary challenge is amenable for use with challenges to multicellular and unicellular organisms such as animals, plant, fungi, bacteria, and the like, to organs of multi-cellular organisms such as epidermis, liver, heart and the like, and to tissues or individual cells or cell cultures such as isolated cells from multi-cellular organisms such as sperm, eggs, white blood cells, neurons, and the like or cultures of such cells. One embodiment of the present invention enhances and/or prolongs the effects of a primary challenge to human epidermis by using a different secondary challenge.

BACKGROUND OF THE INVENTION

Studies on the effects of a challenge (insult) to provoke a human physiological response are needed to understand the etiology of disease and to develop both preventative measures and efficacious treatments. For example, studying the effects of stool on the etiology of diaper rash is needed to develop and/or determine efficacy of products, medications and/or processes that effectively prevent and/or treat diaper rash, which continues to routinely occur among many diapered children. Despite the many studies done to date, the etiology of diaper rash and the mechanisms of various diaper rash preventative and curative agents is incompletely understood. In general, this can be said for most dermatological diseases, as well as many common diseases of other tissues, organs and organisms.

Clinical and non-clinical scientific studies of biological responses, such as of diaper rash and many other dermatological responses, are hindered when current methods and/or devices cannot detect weak responses and/or distinguish among multiple causes for an observed response (i.e., disentangle or interpret a confounded response). Such studies are further hindered when the response being studied, such as diaper rash, occurs with relatively low and unpredictable frequency among the general population.

A common procedure to enhance a weak or inconsistent response is to damage or prime the responsive system prior to challenging it, but the enhanced response is often confounded. For example, the scarification test (Frosch and Kligman, 1976, Contact-Dermatitis 2: 314–242) has long been used to study irritant responses by first physically scarring skin with a needle prior to challenging that damaged skin with substances suspected to have mild irritancy or a weak response. Studies of allergenic and sensitization responses of human skin have long applied this approach by first priming the responsive system with repeated challenges, often over several weeks, to study effects of a second challenge of the same or different type (e.g., Kaidbey and Kligman, 1980, Contact Dermatitis 6:161–169).

There are two concerns with first damaging or priming a responsive system to study responses of that system. First, the damage or modification to the responsive system can cause the responsive system to respond to a challenge by a different mechanism than would the same naïve (undamaged and/or unmodified) responsive system. Second, the degree or severity of the response to a second challenge by a responsive system that has already been damaged or modified can be completely erroneous compared to a naïve responsive system. For example, a second challenge to already damaged skin could result in a severe response when the response by naïve skin would have been nil. Moreover, when the subjects are infants there is heightened justifiable concern anytime a severe response is observed and researchers would rather avoid inducing severe responses by any available means.

A common procedure to minimize confounding of a response, particularly when trying to study mechanisms of disease progression and/or the effects of interventions on the disease or on a injury, is to control the challenge, such as by using direct patching methods in dermatology studies. Such methods, however, are often inadequate when the response occurs at low frequency in the study population and/or the tools used to assess the response are relatively insensitive. To overcome these problems, a direct patching method is often used to study dermatological responses. However, these methods, when they work, typically require lengthy and/or repeated exposures that can be excessive and/or irrelevant to the normal course of events. In addition, many researchers and/or subjects find current patching methods sufficiently inconvenient and costly in time and resources that development of abbreviated methods is desirable.

The present invention is a novel approach to study physiological responses, particularly where enhancing and/or prolonging a response to a challenge without changing the inherent nature of the response is desirable. The methods are useful when the response of interest needs to be studied under both highly controlled and poorly-controlled challenge scenarios. In addition, the present invention reduces the challenge duration needed to provoke an enhanced and/or prolonged response. A specific embodiment of the present invention accomplishes this by enhancing and/or prolonging the effects of the primary challenge (stool) to human epidermis by using a different secondary challenge (tape-stripping) to elicit enhanced and durable erythemic and increased transepidermal water loss (TEWL) responses. In addition, the response to the initial challenge typically corresponds closely to what normally occurs with subjects during their normal lives because the exposure duration is relevant to the common experience of the subjects. Moreover, the primary challenge is applied to healthy, non-damaged skin so that the response is not confounded with the skin's responses to any other pre-damage challenge.

SUMMARY OF THE INVENTION

The present invention relates to a test method to enhance and/or prolong the response of a primary challenge to a responsive system, so that the primary challenge can be better studied, by using a different secondary challenge that does not alter the mechanism by which the primary challenge affects the responsive system nor does it confound the response of the primary challenge. Further, the present invention typically: 1) reduces the exposure duration needed for the primary challenge to induce a response to one that is more relevant to normal exposure scenario(s) for the responsive system or subject, 2) reduces the number of subjects needed to observe statistically significant and/or clinically relevant effects, 3) is more convenient for the researchers, and 4) is minimally stressful to the responsive system or subjects. In addition, the primary and/or secondary challenge may be preceded by one or more interventions in studies designed to understand the etiology of the disease and/or determine the efficacy of a preventative measure. In addition, the secondary challenge may be preceded by and/or followed by one or more interventions in studies designed to determine the efficacy of a curative measure.

DETAILED DESCRIPTION OF THE INVENTION

As used herein, "study" refers to either clinical or non-clinical research with specified testable hypotheses. As used herein, "subject" refers to a human, lower animal species, or other specified organism participating in a study. As used herein, "responsive system" refers to any organism, organ, tissue, mass of cells, or individual cell(s) for which a change in activity, appearance, function, structure, or other condition can be provoked or induced. As used herein, "challenge" refers to the entity and/or process of provoking, moderating or otherwise influencing a physiological (including biochemical) activity by exposure under defined conditions to one or more physical, chemical or biological conditions or actions. As used herein, "test site" refers to any physical location on the responsive system, entity or organism that is monitored during the course of a study. As used herein, "primary challenge" refers to the first challenge applied to one or more test sites, that elicits one or more response(s) (which may or may not be detectable until after the secondary challenge). The primary challenge is the main challenge of interest in the study. There may be more than one component to primary challenge (e.g., there may be a chemical challenge and a physical challenge or there may be two successive identical or different chemical challenges) wherein all components of the primary challenge precede the secondary challenge. As used herein, "secondary challenge" refers to a challenge applied after the primary challenge to one or more test sites designed or intended to enhance and/or prolong the response of the primary challenge. Importantly, a secondary challenge does not confound the response of the primary challenge nor does it alter the mechanism by which the primary challenge elicits a response. As used herein, "confound" means to confuse the meaning or interpretation of an observation even in the presence of controls. As used herein, "enhances" refers to increasing the magnitude or intensity of an entity or event, such as increasing the color intensity or area affected during a dermatological response to a challenge. As used herein, "prolongs" refers to increasing the duration of an event. As used herein, "recovery period" refers to a defined period of time during which the responsive system has opportunity to overcome the effects of a challenge. As used herein, "intervention" refers to any process, act, condition, substance and/or entity attempting to affect the outcome of a challenge, such as to prevent, reverse, and/or attenuate the response of a responsive system to a primary challenge. As used herein, "pre-challenge intervention" refers to any process of exposing a test site and/or control site to one or more physical, chemical or biological conditions prior to exposure to at least one primary challenge. Thus, where there are a series of primary challenges, a pre-challenge intervention can occur anytime so long as it precedes one or more of the primary challenges. As used herein, "post-challenge intervention" refers to any process of exposing a test site and/or control site to one or more physical, chemical or biological conditions subsequent to exposure to any primary challenges. The "post-challenge intervention" can precede one or more secondary challenges, occur between/among one or more secondary challenges, or can follow one or more secondary challenges. As used herein, "concurrent-challenge intervention" refers to any process of exposing a test site and/or control site to one or more physical, chemical or biological conditions during one, or more, of the primary challenger(s). As used herein, "response" refers to any detectable condition or change in condition of a responsive system. For example, a change in visual rash severity or TEWL before and after a challenge is a measure of response to that challenge. The method of detection includes but is not limited to methods utilizing human skills only and/or chemical, physical, mechanical, and/or electrical methods and equipment. As used herein, "assessing" refers to any method of evaluating, observing, noting, and/or comparing the condition (e.g., response) of a test site. As used herein, "pate test grade" refers to a visible skin response scored using a standardized scale (see table 17, page 99 in McNamara, 1976, in "New Concepts in Safety Evaluation", a modification of which is incorporated herein with detailed text). As used herein, "diaper rash" refers to a response indicated by the occurrence on diapered epidermis of what is clinically defined as either erythema or dermatitis, or both, where persistent redness, dryness, pustules and/or other symptoms associated with such conditions may arise. As used herein, "rash" refers to a response indicated by the occurrence on epidermis of what is clinically defined as erythema, dermatitis, psoriasis, or any of several other skin conditions where persistent redness, dryness, papules, pustules and/or other symptoms associated with such conditions may arise. As used herein, "TEWL" refers to trans-epidermal water loss, which is a measure of water movement across and out of the epidermis (skin). TEWL is related to the integrity of skin barrier function when measured under standardized conditions of temperature and humidity after the subject has been sufficiently equilibrated to those standardized conditions. As used herein, "stool" refers to feces from human intestines. As used herein, "stool analog" refers to blends of irritative components commonly found in stool including, but not limited to, SHIME, enzymes, bile acids, candida species and mixtures thereof. As used herein, "SHIME" (Simulation for the Human Intestinal Microbial Ecology) refers to a biologically-simulated human fecal material created in laboratory digestion chambers having a bacterial consortia and both physical and chemical conditions representative of the various segments of the human intestinal tract. SHIME is designed to have representative characteristics of human feces from healthy adults or infants fed a varied diet, but lacks any pathogenic microbes to avoid the spread of disease and lacks any substantive amount of bulking or solidifying components, like cellulose. SHIME is further described in the following two references which are incorporated herein by reference in their entirety: 1. Molly, K., et. al., 1993. Development of a 5-step multi-chamber reactor as a simulation of the human intestinal microbial ecosystem. Appl. Microbiol. Biotechnol. 39:254–263; and 2. De Boever, P., et. al., 200X (in review). Development of a six-stage culture system for simulating the gastrointestinal microbiota of infants. Microb. Ecol. Health Dis. As used herein, "tape-stripping" refers to the act of applying a material of known adhesive properties to skin in a prescribed manner and removing that material for the purposes of subjecting the skin to a physical challenge. Materials of known adhesive properties useful for tape-stripping, which need not specifically be in a tape format, include adhesive tapes such as D-squame® and Sebutape® (CuDerm Corporation, Dallas, Tex.) or Blenderm™ and ScotchTape™

(3M Company, St. Paul, Minn.), and hydrogels such as Hypan® (Hymedix International, Inc., Dayton, N.J.), and other types of materials with adhesive properties such as glues, gums, and resins. As used herein, "control site" or "control" refers to any test site and/or study treatment used to establish a standard of comparison for judging experimental effects and/or the degree of variation in effects, such as those associated with experimental noise, that occur during a study. As used herein, "challenge(d) site" refers to any test site that receives a primary and subsequent secondary challenge. As used herein, "negative control" refers to any control site that is treated identically to a challenged site except it receives neither a primary nor a secondary challenge. For instance, where a responsive system is first cleansed with water and then subjected to a primary and secondary challenge at a given temperature, the control site would also be cleansed with water and would be subject to the same given temperature, but would not be subject to the primary nor secondary challenge. As used herein, "primary control" refers to a control site that receives the primary challenge, but no secondary challenge. A primary control may or may not receive a concurrent-challenge intervention, pre-challenge intervention, or post-challenge intervention. As used herein, "secondary control" refers to a control site that receives the secondary challenge, but no primary challenge. Where beneficial to a study design, a secondary control may receive a post-challenge intervention, even though it has not received a primary challenge. As used herein, "positive control" refers to a control site that receives a substitute primary challenge known to induce a defined response with or without the secondary challenge. All percentages, ratios, and parts herein, in the Specification, Examples, and Claims are by weight unless otherwise stated. The term "$m^2$", as used herein, means square meters. The term "$cm^2$", as used herein, means square centimeters. The term "cm", as used herein, means centimeters. The term "g", as used herein, means gram. The term "ml", as used herein, means milliliter. The term "hr", as used herein, means hour. The term "RH", as used herein, means relative humidity. The term "psi", as used herein, means pounds per square inch. The term "wt", as used herein, means weight. As used herein, the term "comprising" means that the various components, ingredients, or steps, can be conjointly employed in practicing the present invention. Accordingly, the term "comprising" encompasses the more restrictive terms "consisting essentially of" and "consisting of."

A. General Method

The test method of the present invention enhances and/or prolongs one or more of the effects of a primary challenge to a responsive system. The method enables the primary challenge to be better studied by using a different secondary challenge that does not alter the mechanism by which the primary challenge affects the responsive system nor does it confound results of the primary challenge with other spurious responses.

More specifically, the method generally comprises assessing a test site of the responsive system in its pre-challenge condition; subjecting the test site to a primary challenge; preferably but not necessarily, assessing the test site for a response; subjecting the same test site to a secondary challenge, wherein the secondary challenge is designed to enhance and/or prolong a response of the responsive system to the primary challenge, without confounding the response nor altering the mechanism by which the primary challenge elicits a response; and assessing the response subsequent to the secondary challenge. Preferably, the response is assessed at least twice following the secondary challenge, wherein the first assessment is made soon after the secondary challenge, and the second assessment is made after a recovery period. The primary and secondary challenges of the present invention can comprise physical challenges, chemical challenges, and/or biological challenges. The primary and secondary challenges may comprise multiple or complex components (for example, a primary challenge comprising a poorly-defined extract or comprising chemicals A and B dissolved in a buffered matrix and heated to a specific temperature) and/or steps (for example, a primary challenge comprising a first chemical challenge concurrently with or followed shortly thereafter by a second chemical challenge (same or different from the first) to the same test site). However, preferably, but not necessarily, the primary and secondary challenges are single steps (or challenges) in the process. The methods claimed herein also preferably comprise the additional step(s) of subjecting test site(s) to one or more pre-challenge intervention(s), post-challenge intervention(s), and/or concurrent-challenge intervention(s). The introduction of these interventions is useful for determining the ability of the intervention to prevent, cure, heal, and/or reduce disease or injury to a responsive system.

The methods of the present invention typically reduces the exposure duration needed for the primary challenge to induce a response to one that is relevant to normal exposure scenario(s) for the responsive system or subject, and is both minimally stressful to the responsive system and/or subjects and convenient for researchers. As a result, the present invention often significantly shortens the duration of and/or number of subjects needed for studies. In addition, it may enhance a low-level response that can be more easily assessed with current measurement techniques.

Thus, the methods of the present invention are also useful in a study design, also claimed herein, wherein the study comprises the steps of the method as outlined above in addition to comprising the steps of creating one or more controls selected from the group consisting of negative controls, primary controls, secondary controls, positive controls, and mixtures thereof. The studies and/or methods of the present invention are preferably designed to understand of the etiology of a disease and/or the ability of an intervention or challenge to prevent, cure, heal, and/or reduce and/or induce damage or injury to a responsive system.

B. Responsive Systems and/or Subjects

The responsive systems and/or subjects utilized in the methods of the present invention include but are not limited to: multi-cellular and unicellular organisms such as humans, animals, plants, fungi, bacteria, and the like; organs of multicellular organisms such as epidermis, liver, heart and the like; and to tissues or individual cells or cell cultures such as those isolated cells from multi-cellular organisms including but not limited to sperm, eggs, white blood cells, neurons, stoma, and the like.

C. Challenges

The primary and secondary challenges used in the method defined above can be of a physical, chemical, or biological nature. Some examples of physical challenges include, but are not limited to: heat, cold, humidity, desiccation ultraviolet or other forms of radiant energy, dark, friction, abrasion, lubrication, electric or magnetic energy, pressure, vacuum, visual images, occlusion, and sound. Some examples of chemical challenges are any element of the periodic table or non-living compositions of those elements including, but not limited to: organic and inorganic acids and bases or conditions caused by their presence in aqueous systems, surfactants, metal and complexes thereof, salts, proteins, lipids, vitamins, polymers, pharmaceuticals, feces, urine, perspiration, hair, extracts, and/or enzyme digests. Some examples of biological challenges include, but are not limited to: microbials, cells, viruses, bacteria, parasites, and/or other living entities (e.g., fungi known to cause dermatitis, amoeba or protozoa known to cause dysentery or other diseases, mosquitoes or mites known to directly induce a range of responses or indirectly induce a range of responses when they are vectors for the transmission of viruses or parasites).

The methods of the present invention include but are not limited to the embodiments listed below:

1. human skin briefly exposed to ultraviolet radiation and subsequent tape-stripping (physical-physical/primary-secondary challenge) where skin redness and/or TEWL is measured to evaluate the efficacy of a UV-blocking agent applied as a pre-challenge intervention;
2. human skin exposed to trypsin (enzyme) and subsequent tape-stripping (chemical-physical/primary-secondary challenge) where interleukin 1 alpha (IL-1α) induction and/or TEWL is measured to evaluate the efficacy of an enzyme inhibitor applied as a pre-challenge intervention;
3. human skin exposed to *Candida albicans* (fungus) dosed into SHIME and subsequent tape-stripping (biological(and chemical)-physical/primary-secondary challenge) where visual dermatitis and/or TEWL is measured to evaluate the efficacy of a fungal inhibitor applied as a pre-challenge intervention;
4. human skin exposed to trypsin (enzyme) and subsequent acetone exposure (chemical-chemical/primary-secondary challenge) where visual erythema score and/or TEWL is measured to evaluate the efficacy of an enzyme inhibitor applied as a pre-challenge intervention;
5. bovine eye exposed to cosmetic product(s) and subsequent sodium lauryl sulfate exposure (chemical-chemical/primary-secondary challenge) where interleukin 1 alpha (IL-1 a) is measured to evaluate the irritancy of various cosmetic products;
6. ovarian carcinoma cells exposed to treatment chemical (s) and subsequent exposure to growth factors (chemical-biological(or chemical)/primary-secondary challenge) where cellular division is measured by microscopy.

The specific embodiments of combinations of responsive systems exposed to primary and secondary challenges and then measured for various responses are numerous and a complete listing of such combinations is impractical. It is understood that one of ordinary skill in the art will be able to apply the general method of the present invention to suit his/her needs in a wide variety of applications, given the guidance of the present specification and/or examples.

D. Biological and/or Chemical Primary Challenge/Tape-stripping Secondary Challenge One preferred embodiment of the present invention, useful in studies aimed at quickly assessing the effect of a biological and/or chemical substance on a responsive system, such as skin or cell cultures derived therefrom, comprises the steps of: assessing a test site of a responsive system in its pre-challenge condition; subjecting the test site to a primary challenge, wherein the primary challenge comprises a biological and/or chemical challenge; subjecting the test site to a secondary challenge, wherein the secondary challenge comprises the physical challenge of tape-stripping; and assessing the response subsequent to the secondary challenge, preferably at least twice, wherein the first assessment is made soon after the secondary challenge and the second assessment is made after a recovery period. By tape-stripping subsequent to the primary challenge of interest, the response of the responsive system to the primary challenge is enhanced and/or prolonged. Additionally, typically the duration of the application of the primary challenge necessary to provoke a response is substantially reduced.

A preferred embodiment of the invention is a clinical or non-clinical study involving male and/or female subjects of any age during which normal; healthy test sites on each subject are identified, and from which selected challenge sites receive both a primary challenge for a defined period of time and a secondary challenge at a defined period of time after the primary challenge. A variety of appropriate control sites may be established. Some may receive the same primary challenge only (i.e., primary control), or the same secondary challenge only (i.e., secondary control). Others may receive neither a primary nor a secondary challenge (i.e., negative control). Some may receive an appropriate alternative primary challenge (i.e., positive control), which may or may not receive a secondary challenge. The test sites may also receive other types of control interventions as may be required for the interpretation of study results. In the preferred embodiment of the present invention, test sites may be assessed several times to record response(s) that may occur during the study, including, but not limited to the following times: 1) at basal (baseline) conditions prior to the primary challenge, 2) subsequent to the primary challenge, 3) subsequent to the secondary challenge, and 4) subsequent to a recovery period of defined duration after the primary challenge was initiated and subsequent to any secondary challenge.

When this preferred embodiment is used for studies to determine the efficacy of an action, process, substance and/or product (an "intervention") to prevent, induce, reduce or heal an impaired state or disease, the intervention is applied to appropriate test sites before, during, or after the primary or secondary challenge occurs at those test sites. More specifically, the primary and/or secondary challenge may be preceded by one or more pre-challenge or concurrent-challenge interventions in studies to understand the etiology of the impairment or disease and/or determine the efficacy of a preventative measure, or the secondary challenge may be followed by one or more post-challenge or concurrent-challenge interventions in studies to determine the efficacy of a curative measure.

SPECIFIC ILLUSTRATIONS OF A PREFERRED PROTOCOL UTILIZING THE PRESENT INVENTION

This protocol is designed to study the etiology of diaper rash due to skin exposure to stool. It is understood that amendments to the test protocol may be appropriate to study related objectives. The protocol comprises three visits by subjects to a test facility where the study is conducted. The first visit comprises interviewing subjects for possible inclusion in the study, and providing to those subjects who will potentially participate any applicable training and/or materials needed to initiate participation. The first visit is followed by a wash-out period generally comprised of the potential subjects exposing those areas of their skin that are of interest to standardized conditions intended to help minimize experimental noise by eliminating some confounding prior exposures of those skin sites to variable substances, actions and/or environmental conditions. After the wash-out period, the second visit to the test facility comprises re-evaluation of the potential subjects by investigators for inclusion in the study and, if accepted into the study, skin test sites are identified on the subjects which receive challenges for which assessments are made both before and after those challenges to discern skin responses to the challenges or lack thereof. The third visit to the test facility is comprised of assessments made of the challenged skin of subjects to discern persistence of any skin response or lack thereof.

A more specific description of a preferred protocol follows:

First Visit: Subjects are chosen from among healthy infants aged 1 to 36 months, preferably aged 9 to 27 months, and their healthy biological mothers aged 18 to 50 years, preferably 21 to 35 years. Preferably all potential subjects chosen, both adult and child, meet the following inclusion criteria (it is understood that the criteria may change depending upon the study objectives): 1) healthy and evenly-colored skin at all potential test sites with an absence of blemishes, burns, lesions, moles, scars and the like; 2) good general health as determined by having no communicable diseases nor chronic skin or other disorders; 3) neither currently taking nor having taken within two weeks of study initiation any medication(s), either topical or systemic, which in the opinion of the study investigator(s) might influence the skin condition or cause skin rash, such as erythema or dermatitis, or might increase BM frequency (e.g., oral antibiotics, anti-fungal agents, antihistamines, corticosteroids); 4) exhibit no significant hypersensitivity, rash or other abnormal skin reactions or lesions to topical or systemic medications, sunscreens, cosmetics, lotions, creams or fragrances within one year prior to study initiation; and 5) have adequate rash-free area as evaluated by an expert skin grader (i.e., patch test grade is less than 1.0 on a 0 to 4.0 half-point scale) for test sites on the child's buttocks and on the adult's forearms. All potential infant subjects chosen meet the following criteria: 1) child wears disposable diapers full-time; 2) child has no regular occurrence of diarrhea and no diarrhea at least four days prior to nor during the study; and 3) child is preferably transitioning to or already eating table food, where supplementation with formula is acceptable if it constitutes 50% to 99%, preferably 25% to 49%, most preferably 0% to 24% of the diet by caloric intake and where use of table foods and/or prepared baby and toddler foods such as baby cereals and jarred foods comprise the remainder of the diet. All potential adult subjects chosen meet the following criteria: 1) parent is willing to use standard diapers and standard wipes provided on her child instead of their normal brand(s) of diapers and wipes for the duration of the study; 2) parent agrees to use no lotions, creams, ointments, powders, topical medications, or other skin preparations in the diapered area of her child nor any such substance on her own forearm(s) at least 24 hours prior to the first challenge and through to the end of the study; 3) parent agrees to not bath her child's diapered skin area nor bath her own forearms between the primary and secondary challenge of the study, nor bath any such skin areas during the recovery period; 4) parent agrees not to allow her child to consume nor to consume herself any food or beverage containing caffeine at least four hours before any clinical measurement(s) are made; 5) parent agrees not to use nicotine containing products at least 2 hours before clinical measurement(s) are made; and 6) parent must be willing to have her child's buttocks and her own forearm(s) patched with the child's own stool and subsequently have some skin sites tape-stripped.

It is generally understood that only the infant subjects can be studied or only the adult subjects can be studied by making appropriate changes to this general protocol. For example, if only infant subjects are studied, then adults need only participate to the extent necessary to enable study of their children.

Wash-out period: All subjects that meet inclusion criteria during an initial interview are provided with instructions to begin a wash-out period of 24 to 336 hours (1 to 14 days), preferably 72 to 96 hours (3 to 4 days), during which time the child wears exclusively the standard diapers and the parent uses exclusively the standard wipes to clean the child's diapered skin during all diaper changes. Child and adult subjects typically wear their normal clothing and use their normal bathing practices including those soaps, shampoos and the like normally used. During wash-out subjects are not to apply any lotions, creams, ointments, powders, topical medications, and the like on potential test sites 6 to 168 hours prior, preferably 24 to 48 hours prior to the second visit to the test facility. In addition, all subjects are to bathe normally all potential test sites (i.e., baby diapered skin and adult forearms) 0.5 to 6 hours prior, preferably 1 to 2 hours prior to the second visit to the test facility. In addition, it is generally understood that the conditions of the wash-out period are defined by the needs of the study design such that modifications to the methods and materials given herein are acceptable provided they are recorded with a rationale.

Second visit: Subjects report to the test facility for their second visit at pre-determined appointments and the following procedures are performed:

1. Subjects are re-evaluated for suitability for patching against the inclusion criteria and for compliance with instructions for the washout period.
2. Typically, four healthy, unblemished, non-erythemic, non-dermatitic, non-overlapping skin sites approximately 5 cm by 5 cm in size or larger are identified on each infant's buttocks and on one, or both, volar forearm(s) of each mother for use in the study, where the skin sites on each infant are preferably 2 sites located on contralateral (apposing) buttocks and on each mother's forearm are 4 sites located linearly between the wrist and inner elbow. Fewer or additional sites and/or alternative site locations may be chosen as needed to meet the study objectives. The corners of each identified skin site are typically marked using non-toxic, water-soluble marking pens so they can be found during the course of the study.
3. Subjects are sent to a climate-controlled room having a standard temperature (typically 20 to 25° C.) and humidity (typically 40%±5% RH). Subjects' skin sites are typically equilibrated to reach their basal (baseline) conditions by completely exposing their skin sites for 20 to 30 minutes. Longer equilibration time may be used if standardized for all subjects, but shorter equilibration time is often insufficient for most subjects' skin to reach basal conditions.
4. After equilibration, assessments are made in the climate-controlled room at each test site to establish basal conditions of the test sites. Typically assessments are made for erythema by an expert skin grader using a patch grade scoring system (0 to 4.0 half-point scale) and for TEWL using a DermaLab® Evaporimeter with TEWL module (Cortex Technology, Hadsund, Denmark) that measures evaporation rate (g water/m²/hr) and computerized software for automated data collection and analyses (cyberDERM, inc., Media, Pa.). The general procedure for their use is as follows: the evaporimeter probe is applied to each skin site using a standard ring weight that applies equal pressure to all sites and TEWL data are collected for 60 seconds using automatic data collection by a computer linked to the evaporimeter, and where only the final 40 seconds of data are used to calculate a mean TEWL value. Details of operation for both the evaporimeter and software are available in their respective users manuals, which are incorporated herein by reference. In addition, a clean disposable evaporimeter probe cover is used to measure each site to avoid cross-contamination of sites with any challenges and/or interventions applied.

5. The test sites of each subject are randomly assigned to interventions for any combination of challenges, interventions and control conditions to meet the needs of the study design.

6. Stool is sampled from subjects, preferably from infant subjects, 48 to 168 hours, preferably 2 to 48 hours, more preferably 0.5 to 2 hours prior patching the primary challenge during to the second visit. Stool should be collected generally as soon after defecation as possible, such as within 60 minutes, preferably within 15 minutes. Stool can be sampled in various ways such as directly from the perianal grove of the child, from stool in a diaper that is uncontaminated by the diaper materials, or by any other appropriate means that are convenient and pose no harm to the subject. Stool should be sampled with a sterile implement, such as a wood or plastic cervical scraper or popsicle stick, and placed into sample containers, such as clean glass, polyethylene or polypropylene vials with lids. Stool analog such as a synthetic stool, such as SHIME, which is known to be free of pathogenic species, is a possible substitute primary challenge material. Once sampled, stool or SHIME for patching should preferably be stored at approximately 4° C. until needed for preparing patches. Such storage should not exceed 168 hours, preferably not more than 48 hours, more preferably not more than 4 hours prior to patching, most preferably stored and used in patching within 1 hour after defecation.

7. Primary challenge patches are then prepared for subjects. It is preferred that infant subjects are patched with their own stool and parent subjects are patched with their child's stool. The patches are preferably prepared prior to or concurrently with the assignment of skin sites to treatments (although patches could be prepared immediately and stored relative to the guidelines listed above for storing stool). An occlusive square (25.8 $cm^2$) patch is recommended, such as a Hilltop Chamber Systems Patch (a.k.a. Hilltop Chamber Patch, Hilltop Research, Cincinnati, Ohio) consisting of a 2.5 cm diameter nonwoven cotton pad (Webril®) contained within a plastic chamber (e.g., Hilltop Chamber) covered by and held securely to the skin on all sides with an occlusive, hypoallergenic tape (e.g., Durapore®). Non-irritating, hypo-allergenic, occlusive patches made of natural and/or synthetic fibers like as cellulose, rayon or polyolefin may be acceptable alternatives, such as The Former Professional Medical Patch Pad (Kendall Company, Mansfield, Mass.) square of 14.5 $cm^2$ consisting of a nonwoven cotton pad (e.g., Webril®) square of 3.6 $cm^2$ covered by and held securely to skin on all sides with an occlusive, hypoallergenic tape (e.g., Blenderm™, 3M Company, St. Paul, Minn.). Typically patches containing between 0.01 g and 1.0 g per $cm^2$ skin surface, more preferably between 0.25 g and 0.35 g per $cm^2$ skin surface of the stool are sufficient to elicit a desired response. However, it is understood that applying less stool (or less of some other primary challenge) is possible, but this may increase the exposure time necessary to elicit the desired response. Similarly, applying more stool is possible (or more of some other primary challenge) is possible, but this may not be appropriate, practical, economical or pleasant for the subject. Therefore, the amount of stool is not deemed a critical nor limiting aspect of the present invention. The patches may be wetted with between 0.1 g and 1.0 g of distilled and/or deionized water per $cm^2$ skin surface, preferably where the patches may be wetted with between 0.01 g and 1.0 g of synthetic urine per $cm^2$ skin surface, more preferably where the patches may be wetted with between 0.01 g and 1.0 g of natural urine per $cm^2$ skin surface, and most preferably where the patches are unwetted except for liquid associated with the stool applied.

8. Subjects are patched for the primary challenge period for 0.5 to 16 hours, preferably for 1 to 8 hours, more preferably for 3.5 to 4.5 hours, such that the appropriate test sites receive the appropriate randomized interventions assigned in step 5. It is preferred that a standard cleaning method be used prior to applying patches to the skin test sites on child's buttocks and parent's forearm(s), as well as subsequent to removing all patches irrespective of treatment received. A recommended method is to use the standard wipes such that each individual skin test site is wiped 5 times where each time is a single stroke across only that site with the new standard wipe folded in thirds. Once patched, infants may be diapered and all subjects are free to engage in normal activities such as eating, sleeping, playing, etc., provided that the subjects remain at the test facility and avoid strenuous exercise or other activities that might cause perspiration to dislodge patches. In addition, infant subjects will have their diapers changed whenever soiled with stool as well as routinely during the primary challenge, preferably every hour, to avoid moisture accumulation under the patches.

9. Patches from the primary challenge period are removed and each patch site is cleaned using the same standard cleaning method (see 8 above). Subjects' skin is equilibrated (as in 3 above) and assessments of any responses are made (as in 4 above).

10. While subjects are still in the climate control room a secondary challenge of five successive tape-strippings, using five different tapes, is made on test sites receiving the secondary challenge. Preferably the tape is left on for about 1 minute before removal. Tape stripping is preferably performed with D-Square tape (Cu-Derm, Dallas, Tex.), but alternative tapes, such as Blenderm™ (3M Company, St. Paul, Minn.) or equivalent, or other appropriate adhesive materials may be substituted.

11. Tape-stripped test sites are allowed to re-equilibrate for about the same amount of time among all sites and among all subjects, preferably for 10±2 minutes (not to vary by more than two minutes between sites within and among subjects) and assessments of any responses are made (as in 4 above).

12. Subjects leave the test facility and return the next day, preferably 24±2 hours after the primary challenge was initiated. Subjects should not bath nor apply any substances (see inclusion criteria) to the test sites or neighboring skin until the third visit is complete.
13. During the third visit subjects' skin is equilibrated (as in 3 above) and the final assessments of any responses are made (as in 4 above).

EXAMPLES

The following non-limiting examples provide some specific methods of the present invention:

Example 1

The objective of this Example is to study the etiology of diaper rash as potentially induced by exposure to stool. Both infants' buttocks and their respective biological mothers' volar forearms are studied. The use of the secondary tape-stripping challenge allows for a shorter primary challenge duration (4 hours instead of 24 hours) and/or fewer subjects to establish statistically significant findings than studies having the same objective which do not utilize a secondary challenge. The most preferred procedures set forth in the protocol listed above are followed with the following exceptions/details:

The washout stage is 3 days long. The standard diapers used are Pampers Baby-Dry (made with non-lotioned topsheet) and the specific wipes used by the parents and for cleansing test sites during the study are Pampers Baby Fresh One-Ups™ Unscented. Stool is sampled from infant subjects within half an hour of defecation and 1–4 hours prior to patching the primary challenge. Once the patches are prepared the stool is refrigerated whenever patching occurs more than 1 hour after stool sampling. For each subject the four sites are designated for reference. Treatment "A" is a challenge site receiving both a primary and secondary challenge. Treatment "B" is a secondary control receiving a secondary challenge only. Treatment "C" is a primary control receiving a primary challenge only. Treatment "D" is a negative control receiving neither a primary nor secondary challenge. During the primary challenge period, sites B and D receive dry patches whereas sites A and C receive patches containing stool. The test sites are subject to the primary challenge for 4 hours.

Results of using this procedure are presented in Tables 1, 2, 3 and 4. Treatment comparisons were made based on the mean square error from an analysis of variance (ANOVA). With only one minor exception among 40 treatment comparisons made, the following trends occur for both infant buttocks and adult forearm skin:

1. When test sites are assessed after the 4-hour primary patching, stool consistently provokes a significantly greater (but mild) erythemic and TEWL response than do control patches (Treatments A versus B and C versus D are significantly different, but not A versus C).
2. When test sites are assessed after tape-stripping, this secondary challenge has no substantive additional effect in the absence of a prior stool challenge on either erythema score or TEWL, but when a prior stool challenge occurred the tape-stripping has a stronger and consistent directional increased effect on erythema score, but not on TEWL (Treatments A and B comparing post-primary and post-secondary challenge results).
3. When test sites are assessed after the 24-hour recovery period, only the stool plus tape-stripping treatment (A) continues to have a significantly greater (but mild) erythemic and TEWL response than do the other treatments (Treatments A versus B and C versus D and A versus C) whereas skin exposed to all other treatments has returned to very near baseline conditions.

The test is able to demonstrate the following results, despite the small sample size ($N \leq 16$). The combination of the primary and secondary challenges is the only treatment that provokes both an enhanced and prolonged response as assessed by erythema and TEWL. All other treatments return to very near baseline conditions within 24 hours indicating that those treatments cause only transient effects on the skin.

Results of a Study Based on Example 1

TABLE 1

Results for Infant Buttocks - Erythema Patch Grade Score

| Assessment Periods | N | Treatment A Stool + Tape-strip | | Treatment B Tape-strip only | | Treatment C Stool only | | Treatment D: Neither challenge | |
|---|---|---|---|---|---|---|---|---|---|
| | | Mean Response | Std. Err. | Mean Response | Std. Err. | Mean Response | Std. Err. | Mean Response | Std. Err. |
| Baseline | 16 | 0.00 | 0.00 | 0.00 | 0.00 | 0.00 | 0.00 | 0.00 | 0.00 |
| Post-primary challenge | 16 | 1.41 | 0.14 | 0.63 A | 0.16 | 1.50 | 0.11 | 0.59 C | 0.13 |
| Post-second challenge | 15 | 1.83 | 0.14 | 0.93 A | 0.17 | ND | | ND | |
| Post-recovery period | 14 | 0.71 | 0.10 | 0.57 | 0.14 | 0.39 A | 0.12 | 0.39 | 0.11 |

1. Comparisons were made between groups A versus B, C versus D, and A versus C using analysis of variance. Upper case letters indicate unadjusted significance between treatments using ANOVA at 0.05 level.
2. Comparisons were made within treatment between assessment times and baseline using analysis of variance. "*" indicates significance at 0.05 level and "+" indicates significance at 0.10 level.
3. ND = no data

TABLE 2

Results for Infant Buttocks - TEWL (g/m²/hr)

| Assessment Periods | N | Treatment A Stool + Tape-strip | | Treatment B Tape-strip only | | Treatment C Stool only | | Treatment D: Neither challenge | |
|---|---|---|---|---|---|---|---|---|---|
| | | Mean Response | Std. Err. | Mean Response | Std. Err. | Mean Response | Std. Err. | Mean Response | Std. Err. |
| Baseline | 16 | 8.61 | 1.34 | 7.78 | 0.48 | 8.23 | 0.65 | 7.82 | 0.41 |
| Post-primary challenge | 16 | 17.76 | 1.48 | 14.72 A | 2.21 | 20.27 | 2.34 | 13.15 C | 1.70 |
| Post-second challenge | 15 | 18.58 | 1.45 | 12.07 A | 1.17 | ND | | ND | |
| Post-recovery period | 14 | 14.00 | 2.13 | 8.52 A | 0.55 | 8.47 A | 0.89 | 7.60 | 0.37 |

Comparisons were made between groups A versus B, C versus D, and A versus C using analysis of variance.
Upper case letters indicate unadjusted significance between treatments using ANOVA at 0.05 level.
ND = no data.

Results of a Study Based on Example 1 (con't.)

TABLE 3

Results for Female Adult Forearm - Erythema Patch Grade Score

| Assessment Periods | N | Treatment A Stool + Tape-strip | | Treatment B Tape-strip only | | Treatment C Stool only | | Treatment D: Neither challenge | |
|---|---|---|---|---|---|---|---|---|---|
| | | Mean Response | Std. Err. | Mean Response | Std. Err. | Mean Response | Std. Err. | Mean Response | Std. Err. |
| Baseline | 16 | 0.00 | 0.00 | 0.00 | 0.00 | 0.00 | 0.00 | 0.00 | 0.00 |
| Post-primary challenge | 16 | 1.06 | 0.09 | 0.34 A | 0.10 | 1.13 | 0.13 | 0.31 C | 0.09 |
| Post-second challenge | 16 | 1.41 | 0.10 | 0.53 A | 0.10 | ND | | ND | |
| Post-recovery period | 14 | 0.61 | 0.13 | 0.25 A | 0.07 | 0.14 A | 0.06 | 0.11 | 0.06 |

Comparisons were made between groups A versus B, C versus D, and A versus C using analysis of variance.
Upper case letters indicate unadjusted significance between treatments using ANOVA at 0.05 level.
ND = no data.

TABLE 4

Results for Female Adult Forearm - TEWL (g/m²/hr)

| Assessment Periods | N | Treatment A Stool + Tape-strip | | Treatment B Tape-strip only | | Treatment C Stool only | | Treatment D: Neither challenge | |
|---|---|---|---|---|---|---|---|---|---|
| | | Mean Response | Std. Err. | Mean Response | Std. Err. | Mean Response | Std. Err. | Mean Response | Std. Err. |
| Baseline | 16 | 6.31 | 0.42 | 6.66 | 0.50 | 6.46 | 0.48 | 6.56 | 0.62 |
| Post-primary challenge | 16 | 14.04 | 0.84 | 8.39 A | 0.58 | 14.50 | 0.86 | 7.90 C | 0.57 |
| Post-second challenge | 16 | 14.39 | 1.17 | 8.68 A | 0.67 | | | | |
| Post-recovery period | 14 | 10.54 | 1.15 | 7.36 A | 0.53 | 6.80 A | 0.48 | 6.48 | 0.57 |

Comparisons were made between groups A versus B, C versus D, and A versus C using analysis of variance.
Upper case letters indicate unadjusted significance between treatments using ANOVA at 0.05 level.
ND = no data.

Laboratory Patch Test Grading Scale
0.0 No apparent cutaneous involvement.
0.5 Greater than 0, less than 1; ex., faint, barely perceptible erythema or slight dryness (glazed appearance).
1.0 Faint but definite erythema, no eruptions or broken skin or no erythema but definite dryness; may have epidermal fissuring.
1.5 Greater than 1, less than 2; ex., well-defined erythema or faint erythema with definite dryness, may have epidermal fissuring.
2.0 Moderate erythema, may have a few papules or deep fissures, moderate-to-severe erythema in the cracks.
2.5 Greater than 2, less than 3; ex., moderate erythema with barely perceptible edema or severe erythema not involving a significant portion of the patch (halo effect around the edges), may have a few papules or moderate-to-severe erythema.
3.0 Severe erythema (beet redness), may have generalized papules or moderate-to-severe erythema with slight edema (edges well defined by raising).

3.5 Greater than 3, less than 4; ex., moderate-to-severe erythema with moderate edema (confined to patch area) or moderate-to-severe erythema with isolated eschar formations or vesicles.

4 Generalized vesicles or eschar formations or moderate-to-severe erythema and/or edema extending beyond the area of the patch.

Notes

1. The degree of reaction expressed by such descriptive terms as "moderate" and "severe" is, in itself, subjective. Such terminology can be accurately understood only through experience.
2. Any reaction of greater severity than Grade 4 should be described in detail. Unusual reactions not described by the scale should also be described.

Example 2

The objective of this Example is to study the efficacy of a preventative intervention for diaper rash induced by exposure to stool. The use of the secondary tape-stripping challenge allows for a shorter primary challenge duration (4 hours instead of 24 hours) and/or fewer subjects to establish statistically significant findings than studies having the same objective which do not utilize a secondary challenge.

Infants' buttocks and/or their respective biological mothers' volar forearms are studied. Procedures set forth in the protocol listed above are followed with the following exceptions/details:

The study takes the form of a cross-over design. Two groups of subjects are established. Group I receive a pre-challenge intervention of 15% petrolatum ointment applied to all sites 2 hours prior to the primary challenge and Group II serves as the control group receiving no such intervention. After all assessments are made, subjects from both groups enter a second wash-out period identical to the first. Subjects then receive the opposite treatment; i.e., Group I serves as the control group and Group II as the intervention group. The same treatments and assessments are again made on the two groups.

Example 3

The objective of this Example is to study the efficacy of a curative intervention for diaper rash induced by exposure to stool. Infants' buttocks and/or their respective biological mothers' volar forearms are studied. The use of the secondary tape-stripping challenge allows for a shorter primary challenge duration (4 hours instead of 24 hours) and/or fewer subjects to establish statistically significant findings than studies having the same objective which do not utilize a secondary challenge.

The preferred procedures set forth in the protocol listed above are followed with the following exceptions/details:

The study takes the form of a cross-over design. Two groups of subjects are established. Group I receive a post-challenge intervention of ZnO ointment, such as (Desitin®), applied to all sites 15 minutes after post-secondary challenge assessments are made and Group II serves as the control group receiving no such intervention. After all assessments are made subjects from both groups enter a second wash-out period identical to the first. Subjects then receive the opposite treatment; i.e., Group I serves as the control group and Group II the intervention group. The same treatments and assessments are again made on the two groups.

Example 4

The objective of this Example is to compare the efficacy of two preventative interventions for sunburn induced by exposure to UVB radiation. Adult upper backs and/or upper arms are studied. The use of the secondary tape-stripping challenge allows for a shorter UVB exposure necessary to adequately meet the objectives of the study. Preferred procedures set forth in the protocol listed above are followed with the following exceptions/details:

The wash-out period is typically 96 hours during which no lotions, creams, ointments, powders, topical medications, or other skin preparations are applied to the subject' backs and/or upper arms, and those areas are clothed whenever the subjects might be exposed to daylight. The study takes the form of a cross-over design. Two groups of subjects are established, one for each sunscreen. Each group receives a pre-challenge intervention of their respective sunscreens applied to all test sites 1 hour prior to the primary challenge. The primary challenge to two of the four test sites for each subject consists of a three minute exposure to a 1600 watt high pressure xenon arc lamp with a Schott WG1 filter. The secondary challenge is the same five tape-strippings with D-squame tapes to one primary-challenged site and to the secondary control site. After all assessments are made subjects from both groups return two weeks later and enter a second wash-out period identical to the first. Subjects then receive the opposite intervention they receive during the first run. The same treatments and assessments are again made on the two groups.

Example 5

The objective of this Example is to study the etiology of diaper rash induced by exposure to a surrogate stool, SHIME, compared to a mixture of components thereof containing bile acids (cholic, chenodeoxycholic, deoxycholic, lithocholic) and enzymes (chymotrypsin, trypsin, lipase) on adult upper arms. The use of the secondary tape-stripping challenge allows for a shorter primary challenge duration (4 hours instead of 24 hours) and/or fewer subjects to establish statistically significant findings than studies having the same objective which do not utilize a secondary challenge. The procedures set forth in the protocol listed above are followed with the following exceptions/details:

Adult subjects are recruited from the general population. Subjects chosen should meet inclusion criteria established for Example 1. Upper arms of adult females aged 18 to 50 are studied after a washout period of seven days during which no applications of lotions, creams, ointments, or other applications have been made. Each upper arm for each subject is assigned randomly to a different treatment group. Group I receives SHIME as the primary challenge and the other receives the component mixture. The primary challenge is applied for four hours using occlusive patches. The secondary challenge is successive tape stripping. In addition to the clinical assessments (visual irritation, TEWL) made on subjects, sub-samples of SHIME are analyzed to determine differences in their biological and/or chemical composition from those of the bile acids/enzymes mixture, and those analytical results are compared to the clinical assessments from the challenge experiment.

Example 6

The objective of this Example is to determine the efficacy of an aloe-containing lotion on treating damaged skin. The Example follows the procedures of Example 5 and therefore provides the same time-saving and reduced subject number advantages via the use of tape-stripping. The Example employs an additional post-challenge intervention subsequent to the final tape-stripping comprising the application of an aloe-containing lotion to some of the test sites. Those test sites not receiving the lotion are controls. Following a recovery period of 3 hours, all test sites are assessed (visual irritation, TEWL).

Example 7

The objective of this Example is to enhance detection of a delayed hypersensitivity response by a substance of low reactivity; i.e., one that elicits a weak or infrequent sensitization response among the general population. Such studies are necessary to evaluate such substances for use in formulations of products that can contact the skin of consumers. The primary challenge to skin comprises multiple exposures to a chemical (e.g., parabens or derivatives thereof) suspected to invoke skin sensitization. The chemical secondary challenge enhances the primary response sufficiently to reduce the number of subjects needed to meet the objectives of the study; i.e., identify subjects who elicit a sensitization response that would otherwise be missed by current methods unless.

Adult subjects are recruited from the general population. Subjects chosen should 1) be in general good health as determined as having no communicable disease, asthma, nor chronic skin or other disorders, 2) have no skin lesions, rash, scars or other skin abnormalities within the skin test site area, 3) not be receiving immunosuppressive drugs, allergy injections or other medications that in the Investigator's judgment might confound the subjects response to the challenge, and 4) not have confirmed skin sensitization as result of participation in a prior dermal clinical study.

The primary challenge is applied to the skin and covered with an occlusive patch. Challenges can be made using semi-occlusive or semi-open dermatological. patches, or as on open application without a patch depending on the nature of the primary chemical challenge and expected usage scenario. Patches are applied to the lateral surface of the upper arm and each site is marked so that the repeat primary challenge is applied to the same location.

The primary challenge is applied every Monday, Wednesday and Friday for three consecutive weeks, with each primary challenge/patch worn for 24 hours. Following three weeks of primary challenge the subjects are given a two week rest period where no challenges are given followed by a final primary challenge for 24 hours to the same skin test site on the subject. Upon completion of the final primary challenge a standardized secondary challenge of acetone (neat) is swabbed onto the test sites. The skin is then assessed immediately and daily thereafter for four days for delayed contact hypersensitivity using visual scoring.

Example 8

The objective of this Example is to study the ability of a low to moderate abrasive material to elicit skin irritation. Adult volar forearm is exposed to a physical primary challenge with multiple exposures. The same conditions of recruitment and patch procedures from Example 7 apply. The primary challenge, for example, rubbing a non-woven fabric in a circular motion, is applied four times daily for one minute each time and repeated for four days. Upon completion of the last primary challenge a neat acetone secondary challenge is applied by swabbing the test site(s). The skin is assessed for an irritation response one hour post secondary challenge and once per day during the next 48 hours. The use of the secondary challenge enhances the response sufficiently to adequately meet the objectives of the study with a reduced number of subjects compared to current methods.

Example 9

The objective of this Example is to evaluate the efficacy of a concurrent intervention to prevent an irritation response in human infant and/or adult diapered skin exposed to multiple physical (e.g., humidity, material abrasion), chemical (e.g., surfactant), and/or biological-chemical (e.g., stool) primary challenges. The use of the secondary challenge involving heat allows for an enhanced response sufficiently to meet the objectives of the study.

Infant and/or adults that normally wear disposable or cloth diapers would be eligible for this study provided they meet the inclusion criteria in Example 7. Subjects participate in a wash-out period of 4 days, though as few as one and as many as 21 days may be required depending on the nature of the study. The washout period is similar to that specified in Example 1. Following the wash-out period subjects are given a baseline evaluation for skin condition by visual grading.

Subjects are randomized into two groups, each receiving the primary challenge nearly continuously, with the exception of diaper changes and bathing, for four consecutive days comprising exposure to multiple primary challenges that occur naturally in the diaper, such as urine, feces, occlusion, material abrasion, cleaning, etc. One group continues to wear the control diaper during the primary challenge period and the other group wears a diaper containing a petrolatum-based ointment which is applied to the skin during normal wear. In this Example the petrolatum-based ointment is included as a concurrent intervention.

At the end of the primary challenge phase all subjects are exposed to a secondary challenge, heat. Subjects stay in a controlled temperature room of high heat (85±5° F.) and humidity (85±5% RH) for 60 minutes. Following the secondary challenge the subject' skin is assessed immediately, after one hour, and daily thereafter over 48 hours by visual grading.

Example 10

This example is essentially identical to Example 9 and includes a second secondary challenge and optional assessment techniques. The objectives and procedures are the same throughout with the following exceptions.

After the secondary challenge and post-secondary challenge assessment (both immediate and one hour thereafter), a second secondary challenge of tape-stripping is applied. The tape strips are immediately frozen (−70° C.) for later analyses of interleukin 1 alpha(IL-1α). Test sites are visually assessed after 10 minutes post-secondary challenge and daily thereafter for 48 hours.

What is claimed is:

1. A method of enhancing and/or prolonging a response to a primary challenge to a responsive system comprising the steps of:
   a) subjecting a test site of the responsive system to the primary challenge;
   b) assessing the test site for the response;
   c) subjecting the test site to a secondary challenge, wherein the secondary challenge differs from the primary challenge and wherein the secondary challenge is designed to enhance, and/or prolong the response of the responsive system to the primary challenge; and
   d) assessing the response using a means selected from the group consisting of visual evaluation using a predefined scale and TEWL;

wherein the primary challenge is a chemical challenge and the secondary challenge is a physical challenge the physical challenge being selected from the group consisting of heat, cold, humidity, desiccation, tape stripping, friction, abrasion, lubrication, pressure vacuum, occlusion, sound and combinations thereof.

2. The method according to claim 1 further comprising the steps of subjecting the test site to at least one pre-challenge intervention.

3. The method according to claim 1 further comprising the steps of subjecting the test site to at least one intervention selected from the group consisting of concurrent-challenge intervention, post-challenge intervention, and mixtures thereof.

4. The method according to claim 1 wherein assessing the response comprises TEWL measurement.

5. A study utilizing enhanced and/or prolonged responses to a primary challenge to a responsive system comprising the steps of:
   a) applying the primary challenge to a test site of the responsive system; assessing the test site for a response; applying a secondary challenge to the test site, wherein the secondary challenge differs from the primary challenge and wherein the secondary challenge is designed to enhance and/or prolong a response of the responsive system to the primary challenge, wherein the primary challenge is a chemical challenge and the secondary challenge is a physical challenge that is selected from the group consisting of heat, cold, humidity, desiccation, tape stripping, friction, abrasion, lubrication, pressure, vacuum occlusion, sound and combinations thereof; and
   b) creating one or more controls selected from the group consisting of negative controls, primary controls, secondary controls, positive controls, and mixtures thereof;
   c) assessing a primary challenge response subsequent to the primary challenge and prior to the secondary challenge using a means selected from the group consisting of visual evaluation using a predefined scale and TEWL;
   d) assessing at least one secondary challenge response one or more times after the secondary challenge using a means selected from the group consisting of visual evaluation using a predefined scale and TEWL;
   e) assessing at least one control response to the controls at the same approximate times as the primary challenge assessment and secondary challenge assessments are made using a means selected from the group consisting of visual evaluation using a predefined scale and TEWL;
drawing conclusions based upon the assessments.

6. The study according to claim 5 comprising at least one additional step comprising subjecting the test site and/or one or more controls to at least one pre-challenge intervention.

7. The study according to claim 5 comprising at least one additional step selected from the group consisting of subjecting the test site and/or one or more controls to at least one concurrent-challenge intervention, and/or subjecting the test site and/or the one or more controls to at least one post-challenge intervention.

8. The method according to claim 1 wherein the secondary challenge is tape-stripping.

9. The method according to claim 1 wherein the primary challenge comprises more than one component and/or step.

10. The method according to claim 1 wherein the chemical challenge is applied to the test site via a patch.

11. The method according to claim 10 wherein the test site is skin.

12. The method according to claim 11 wherein the chemical challenge comprises applying stool and/or stool analog.

13. The method according to claim 12 wherein the test site is subject to the primary challenge for up to about 24 hours.

14. A clinical study designed to assess affects of chemicals on preventing and/or treating diaper rash comprising the method according to claim 11.

15. The method of claim 12 wherein the test site is an adult's forearm and the primary challenge is stool.

* * * * *

UNITED STATES PATENT AND TRADEMARK OFFICE
CERTIFICATE OF CORRECTION

PATENT NO. : 6,756,032 B1
DATED : June 29, 2004
INVENTOR(S) : Bruce Ernest Tepper et al.

It is certified that error appears in the above-identified patent and that said Letters Patent is hereby corrected as shown below:

Column 4,
Line 7, delete "challenger(s)" and insert -- challenge(s) --.
Line 17, delete "pate" and insert -- patch --.

Column 7,
Line 3, delete "arc" and insert -- are --.

Column 8,
Line 11, delete "normal;" and insert -- normal, --.

Column 18,
Line 9, delete "subject" and insert -- subjects' --.
Line 21, delete "arc" and insert -- are --.

Column 21,
Line 3, delete "pressure" and insert -- pressure, --.
Line 29, delete "vacuum" and insert -- vacuum, --.

Signed and Sealed this

Twenty-fourth Day of January, 2006

JON W. DUDAS
*Director of the United States Patent and Trademark Office*